US008398638B2

(12) United States Patent
Alleyne et al.

(10) Patent No.: US 8,398,638 B2
(45) Date of Patent: Mar. 19, 2013

(54) METHOD OF TREATING SPINAL INTERNAL DISK DERANGEMENT

(75) Inventors: Neville Alleyne, La Jolla, CA (US); Stuart Young, Del Mar, CA (US)

(73) Assignee: SpineOvations, Inc., San Diego, CA (US)

( * ) Notice: Subject to any disclaimer, the term of this patent is extended or adjusted under 35 U.S.C. 154(b) by 1653 days.

(21) Appl. No.: 11/215,809

(22) Filed: Aug. 30, 2005

(65) Prior Publication Data

US 2006/0074424 A1 Apr. 6, 2006

Related U.S. Application Data

(60) Provisional application No. 60/605,709, filed on Aug. 30, 2004.

(51) Int. Cl.
 *A61F 2/44* (2006.01)
(52) U.S. Cl. .................. 606/76; 435/403; 623/17.16
(58) Field of Classification Search .................. 606/76, 606/907; 623/17.12, 17.16; 435/403
 See application file for complete search history.

(56) References Cited

U.S. PATENT DOCUMENTS

| | | | |
|---|---|---|---|
| 2,474,911 A | 7/1949 | Pierce et al. | |
| 4,526,909 A | 7/1985 | Urist | |
| 4,837,285 A | 6/1989 | Berg et al. | |
| 5,024,659 A * | 6/1991 | Sjostrom | 604/110 |
| 5,134,122 A | 7/1992 | Orsolini | |
| 5,171,279 A * | 12/1992 | Mathews | 128/898 |
| 5,258,028 A | 11/1993 | Ersek et al. | |
| 5,286,763 A | 2/1994 | Gerhart et al. | |
| 5,290,271 A | 3/1994 | Jernberg | |
| 5,344,452 A | 9/1994 | Lemperle | |
| 5,352,715 A | 10/1994 | Wallace et al. | |
| 5,571,182 A * | 11/1996 | Ersek et al. | 623/23.73 |
| 5,599,852 A | 2/1997 | Scopelianos et al. | |
| 5,641,514 A | 6/1997 | Cho | |
| 5,922,025 A | 7/1999 | Hubbard | |
| 6,107,466 A | 8/2000 | Hasan et al. | |
| 6,129,761 A | 10/2000 | Hubbell | |
| 6,160,033 A | 12/2000 | Nies | |
| 6,183,518 B1 * | 2/2001 | Ross et al. | 623/17.16 |
| 6,264,659 B1 | 7/2001 | Ross et al. | |
| 6,264,695 B1 * | 7/2001 | Stoy | 623/17.16 |
| 6,284,872 B1 | 9/2001 | Celeste et al. | |
| 6,309,420 B1 * | 10/2001 | Preissman | 623/16.11 |
| 6,335,028 B1 | 1/2002 | Vogel et al. | |
| 6,355,705 B1 | 3/2002 | Bond et al. | |
| 6,383,200 B1 | 5/2002 | Wotton, III | |
| 6,391,059 B1 | 5/2002 | Lemperle et al. | |
| 6,432,437 B1 | 8/2002 | Hubbard | |
| 6,468,274 B1 | 10/2002 | Alleyne et al. | |
| 6,652,883 B2 | 11/2003 | Goupil et al. | |
| 6,713,527 B2 | 3/2004 | Bond et al. | |
| 7,060,103 B2 | 6/2006 | Carr et al. | |
| 7,131,997 B2 | 11/2006 | Bourne | |
| 7,306,627 B2 | 12/2007 | Tanagho et al. | |
| 7,341,601 B2 | 3/2008 | Eiserman et al. | |
| RE41,286 E | 4/2010 | Atkinson et al. | |
| 8,127,770 B2 | 3/2012 | Alleyne et al. | |
| 2002/0045942 A1 * | 4/2002 | Ham | 623/17.12 |
| 2002/0176893 A1 | 11/2002 | Wironen et al. | |
| 2003/0009235 A1 | 1/2003 | Manrique et al. | |
| 2003/0149490 A1 * | 8/2003 | Ashman | 623/23.71 |
| 2003/0158607 A1 | 8/2003 | Carr et al. | |
| 2003/0211083 A1 | 11/2003 | Vogel | |
| 2003/0236573 A1 | 12/2003 | Evans et al. | |
| 2004/0024465 A1 | 2/2004 | Lambrecht et al. | |
| 2004/0054414 A1 * | 3/2004 | Trieu et al. | 623/17.16 |
| 2004/0115240 A1 | 6/2004 | Narhi et al. | |
| 2005/0031666 A1 | 2/2005 | Trieu | |
| 2005/0100510 A1 * | 5/2005 | Falco | 424/9.36 |
| 2006/0002971 A1 | 1/2006 | Saltzman et al. | |
| 2006/0052795 A1 | 3/2006 | White | |
| 2006/0074424 A1 | 4/2006 | Alleyne et al. | |
| 2006/0093644 A1 | 5/2006 | Quelle et al. | |
| 2006/0206116 A1 | 9/2006 | Yeung | |
| 2006/0263830 A1 | 11/2006 | Grinstaff et al. | |
| 2008/0096976 A1 | 4/2008 | Alleyne | |
| 2008/0124371 A1 | 5/2008 | Turos et al. | |
| 2008/0160060 A1 | 7/2008 | Ellies | |
| 2008/0166386 A1 | 7/2008 | Caseres et al. | |
| 2008/0299172 A1 | 12/2008 | Young et al. | |
| 2009/0074728 A1 | 3/2009 | Gronthos et al. | |
| 2010/0004699 A1 | 1/2010 | Alleyne et al. | |
| 2010/0004700 A1 | 1/2010 | Alleyne | |
| 2010/0010549 A1 | 1/2010 | Alleyne et al. | |
| 2010/0316715 A1 | 12/2010 | Andersson | |
| 2011/0230919 A1 | 9/2011 | Alleyne | |

FOREIGN PATENT DOCUMENTS

| | | |
|---|---|---|
| EP | 1 410 810 B1 | 1/2007 |
| JP | 5-508795 | 12/1993 |
| JP | 2002-505308 | 2/2002 |
| WO | WO 92/10982 | 7/1992 |
| WO | WO 98/40113 | 9/1998 |

(Continued)

OTHER PUBLICATIONS

International Preliminary Report on Patentability dated Mar. 8, 2007.
Cohen et al., Artecoll—A Long-Lasting Injectable Wrinkle Filler Material: Report of a Controlled, Randomized, Multicenter Clinical Trial of 251 Subjects, Plastic Reconst. Surg., (2004) vol. 114(4), 964-976.

(Continued)

*Primary Examiner* — Kevin T Truong
*Assistant Examiner* — Christian Sevilla
(74) *Attorney, Agent, or Firm* — Knobbe Martens Olson & Bear LLP

(57) ABSTRACT

A method of treating a spinal disk according to the present invention can include inserting an alloplastic bulking agent into the spinal disk to treat the defect. The alloplastic bulking agent has a plurality of microparticles. The bulking agent results in at least one of sealing the defect, increasing a pressure of the disk, increasing a height of the disk, improving stability of the disk and improving structural integrity of the disk.

7 Claims, No Drawings

FOREIGN PATENT DOCUMENTS

| | | |
|---|---|---|
| WO | WO99/44643 | 9/1999 |
| WO | WO 00/44808 | 8/2000 |
| WO | WO 0044394 | 8/2000 |
| WO | WO 02/04007 A2 | 5/2002 |
| WO | WO 02/062404 * | 8/2002 |
| WO | WO02062404 A2 * | 8/2002 |
| WO | WO 03/049669 | 6/2003 |
| WO | WO 2004/026189 | 4/2004 |
| WO | WO 2005/046746 | 5/2005 |
| WO | WO 2008/005676 | 1/2008 |

OTHER PUBLICATIONS

Carruthers, Artecoll®—an injectable micro-implant for longlasting soft tissue augmentation, Skin Therapy Letter, (1999), vol. 4(2), 1-2.

Artecoll Product History. Downloaded from www.artecoll.com on Jun. 2, 2010, pp. 1-2.

Bayston, et al., "The sustained release of antimicrobial drugs from bone cement. An appraisal of laboratory investigations and their significance," *J. Bone Joint Surg. (Br)*, (1982) 64(4):460-464.

Faught, W.E. and Lawrence, P.F. "The effects of laser energy on the arterial wall." Annals of Vascular Surgery 4 (1990); 198-207.

Masala, et al., Percutaneious Vertebroplasty in Painful Schmorl Nodes, Published Online Nov. 18, 2005, Cardiovasc Intervent Radiol 29:97-101.

Wahlig, et al., "Pharmacokinetic study of gentamicin-loaded cement in total hip replacements. Comparative effects of varying dosage," *J. Bone Joint Surg. (Br)*, (1984) 66(2):175-179.

Office Action dated Sep. 26, 2008 in U.S. Appl. No. 11/215,300.

Office Action dated Apr. 1, 2009 in U.S. Appl. No. 11/215,300.

Office Action dated Sep. 9, 2009 in U.S. Appl. No. 11/215,300.

Office Action dated Jun. 9, 2010 in U.S. Appl. No. 11/215,300.

Office Action dated Jul. 20, 2010 in Australian Patent Application No. 2005279772.

Office Action dated Sep. 6, 2011 in Japanese Patent Application No. 2007-530372.

* cited by examiner

METHOD OF TREATING SPINAL INTERNAL DISK DERANGEMENT

CROSS REFERENCE TO RELATED APPLICATIONS

This application claims priority under 35 U.S.C. Section 119(e) to U.S. Provisional Application 60/605,709 filed on Aug. 30, 2004. The entire content of this provisional application is hereby incorporated by reference into this application.

BACKGROUND OF THE INVENTION

1. Field of the Invention

The present invention relates generally to surgical implants and, more particularly, relates to alloplastic spinal disk implants and procedures.

2. Description of the Related Art

Spinal disks comprise a central region called the nucleus pulposus surrounded by a second region known as the annulus fibrosis. The annulus fibrosis portion comprises collagen fibers that may weaken, rupture, or tear, leading to compromised annular confinement of the nucleus and producing disk bulges, herniations and other disk pathologies.

The major causes of persistent, often disabling, back pain are disruption of the spinal disk annulus fibrosis, chronic inflammation of the spinal disk (e.g., herniation), or relative instability of the vertebral bodies surrounding a given spinal disk, such as the instability that often occurs due to a degenerative disease. Spinal disks mainly function to cushion and tether the vertebrae, providing flexibility and stability to the patient's spine. Functionally speaking, spinal disks comprise a central hydrostatic cushion, the nucleus pulposus, surrounded by a containing multi-layered ligament, the annulus fibrosis. As spinal disks degenerate, they can, for example, lose their water content and height which brings the vertebrae closer together. This phenomena results in a weakening of the shock absorption properties of the spinal disk and a narrowing of the nerve openings in the sides of the spine which may pinch the nerve. This spinal disk degeneration can eventually cause back and leg pain. Weakness in the annulus fibrosis from degenerative spinal disks, or from spinal disk injury, can allow fragments of nucleus pulposus within the spinal disk space to migrate into the spinal canal. There, displaced nucleus pulposus or protrusion of annulus fibrosis, e.g., herniation, may impinge on spinal nerves. The mere proximity of the nucleus pulposus or a damaged annulus fibrosis to a nerve can cause direct pressure against the nerve, resulting in numbness and weakness of leg muscles.

It is estimated that approximately 80% of the population at some time in their life suffer back injuries necessitating consultation from a medical doctor for treatment of back pain. A good portion of these back injuries are related to spinal disk protrusions or herniations, and a smaller percentage are related to internal disk derangement.

Often, inflammation from spinal disk protrusions or herniations can be treated successfully by non-surgical means, such as rest, therapeutic exercise, oral anti-inflammatory medications or epidural injection of corticosteroids. In some cases, the spinal disk tissue is irreparably damaged, thereby necessitating removal of a portion of the spinal disk or the entire spinal disk to eliminate the source of inflammation and pressure. At the present time, a procedure which is performed as an open procedure is called a microdiskectomy in which small midline incision is made in the lumbar spine with the dissection being carried down to the lamina. The lamina is then prepared with a keyhole laminotomy, and the ligamentum flavum is then removed. Once this occurs the cal sac and nerve root are retracted to the contralateral side, thus providing exposure to the disk space. Intraoperative lateral x-ray can be implemented to confirm the position of the disk, and direct visualization of the herniation can be noted. Typically, a 15-blade is used to make an annulotomy, and the removal of the herniated fragment or fragments is then undertaken. In some cases this completes the disk excision procedure, while in other cases the surgeon actually places a pituitary rongeur or ring curette into the disk space and removes additional disk material, but a subtotal diskectomy is performed. At the conclusion of the surgery, the offending disk fragment or fragments has been removed, and there is now an annular defect that varies in size. This defect may be as small as 0.5 mm×0.5 mm and as large as 10 mm×15 mm. Typical annulotomies, however, are approximately 5 mm×5 mm. Many current technologies fail to offer surgeons plugs or other materials to place into the disk space for preventing recurrent disk herniation.

To overcome the disadvantages of traditional traumatic spine surgery, minimally invasive spine surgery was developed. Endoscopic spinal procedures, for example, are less invasive than open spinal procedures. In an endoscopic procedure, the spinal canal may not be violated and therefore epidural bleeding with ensuring scarring may be minimized or avoided. In addition. the risk of instability from ligament and bone removal is generally lower in endoscopic procedures than with open diskectomy. Further, more rapid rehabilitation facilitates faster recovery and return to work. Minimally invasive techniques for the treatment of spinal diseases or disorders include diskography, chemonucleolysis, laser techniques and mechanical techniques. These procedures generally require the surgeon to form a passage or operating corridor from the external surface of the patient to the spinal disk(s) for passage of surgical instruments, implants and the like. Typically, the formation of this operating corridor requires the removal of soft tissue, muscle or other types of tissue depending on the procedure (e.g., laparascopic, thoracoscopic, arthroscopic, back, etc.). Once the operating corridor is established, the nerve root may be retracted and a portion or all of the spinal disk removed. Following removal, typical techniques do not implement an annular sealant or other means to efficiently and effectively treat the annular defect or opening to minimize the possibility of recurrent complications such as, for example, future nuclear herniations.

SUMMARY OF THE INVENTION

In accordance with one aspect of the present invention, methods are provided for treating and sealing invertebrate spinal disks that have tears or fissures on the annulus fibrosus.

In one embodiment, a method of treating a spinal disk comprises delivering an agent to the spinal disk, wherein the agent comprises a plurality of microparticles.

In another embodiment, a medical kit comprises an agent comprising microparticles and one or more surgical tools configured for repairing at least one spinal disk.

In another embodiment, an implant agent comprises a plurality of microparticles, for use in repairing and/or improving structural integrity of spinal disks.

In addition, a method of treating a spinal disk comprises placing a plurality of particles into an interior portion of the spinal disk.

DETAILED DESCRIPTION OF THE INVENTION

Any feature or combination of features described herein are included within the scope of the present invention provided that the features included in any such combination are not mutually inconsistent as will be apparent from the context, this description, and the knowledge of one skilled in the art. In addition, any feature or combination of features may be specifically excluded from any embodiment of the present invention. For purposes of summarizing the present invention, certain aspects, advantages and novel features of the present invention are described herein. Of course, it is to be understood that not necessarily all such aspects, advantages or features will be embodied in any particular embodiment of the present invention.

In reference to the disclosure herein, for purposes of convenience and clarity only, directional terms, such as, top, bottom, left, right, up, down, upper, lower, over, above, below, beneath, rear, and front, may be used. Such directional terms should not be construed to limit the scope of the invention in any manner. It is to be understood that embodiments presented herein are by way of example and not by way of limitation. The intent of the following detailed description, although discussing exemplary embodiments, is to be construed to cover all modifications, alternatives, and equivalents of the embodiments as may fall within the spirit and scope of the invention.

The present invention provides compositions and methods for selectively treating defects within or on a spinal disk. These procedures include laminectomy/diskectomy procedures for treating herniated spinal disks, decompressive laminectomy for stenosis in the lumbosacral and cervical spine, medial facetectomy, posterior lumbosacral and cervical spine fusions, treatment of scoliosis associated with vertebral disease, foraminotomies to remove the roof of the intervertebral foramina to relieve nerve root compression and anterior cervical and lumbar discectomies. These procedures may be performed through open procedures (e.g., laminotomy, laminectomy, hemilaminotomy and hemilaminectomy), or using minimally invasive techniques, such as thoracoscopy, arthroscopy, laparoscopy, diskography (e.g., performed percutaneously through a posterior, posterolateral, lateral, anterior or anterolateral approach to the spinal disk) or the like.

According to one implementation of the biocompatible alloplastic implant of the present invention, a condition known as internal disk derangement or annular fissures can on occasion be detected using magnetic resonance imaging (MRI), but in certain instances may more readily be discerned using computed tomography (CT) diskography. These annular fissures or tears can lead to persistence in back pain, and eventually can lead to frank herniations and/or lumbar segmental instability. Such changes that may be seen on MRI are sometimes further evaluated with provocative CT diskography which reveals the location of the annular tear or tears. Procedures such as IDET (intradiscal electrothermal annuloplasty) and nucleoplasty have become more prevalent. Use of the biocompatible alloplastic implant as described herein in these contexts can entail insertion by the interventional radiologist, anesthesiologist, physiatrist or surgeon to facilitate the sealing or other treating of the annular tear from the inside out of the spinal disk.

In accordance with an aspect of the present invention, a biocompatible alloplastic implant is provided for sealing tears or other defects or conditions of a spinal disk, such as a rent in the annulus fibrosis of a spinal disk. The biocompatible alloplastic implant can be inserted into a ruptured spinal disk, filling a portion of the nucleus pulposus and/or annulus fibrosis and providing a seal. In one implementation, the biocompatible alloplastic implant is inserted into a center region of the ruptured spinal disk. According to certain aspects, the biocompatible alloplastic implant is inserted into the nucleus pulposus after a microdiscectomy which closes the iatrogenic rent or annulotomy that the surgeon creates thereby minimizing the risk for recurrent herniation, or is administered as an injectable sealant into the center of the spinal disk, for example, after a diskography procedure in order to seal one or more annular tears.

To the extent such tears or defects are treated using the present invention, risks for recurrent spinal disk herniations and possible revision surgeries can be attenuated or eliminated. Such revisions typically entail slightly larger incisions, greater bony resection, removal of scar tissue, more difficult retraction, increased bleeding, increased anesthetic time, and increased risk for battered nerve roots or possible injury to the dura or root sleeves resulting in potential Cerebro-Spinal Fluid (CSF) leak, fistula, infection, etc. As a result of the minimized need for revision surgery, surgical outcome can be improved and the need for repeat surgery at the same level can be decreased.

Moreover, with the perhaps increased use of provocative diskography to ascertain, for example, whether adjacent segments above or below a planned fusion need to be incorporated, a user can instill the biocompatible alloplastic implant to minimize the extension of the fusion to the adjacent segment. Using conventional procedures, for example, if an unstable motion segment were planned to be fused and preoperative provocative diskography revealed the adjacent segment (e.g., the adjacent spinal disk) as also being symptomatic, that level would be included in the fusion mass. However, in accordance with an aspect of the present invention, the biocompatible alloplastic implant of the present invention can be instilled into the adjacent segment prior to the surgery to help seal the annular tear or tears. In one implementation, the biocompatible alloplastic implant of the present invention can be instilled into the adjacent segment during the preoperative provocative diskography. As a result, the use of the present biocompatible alloplastic implant is not limited to microdiscectomy or open diskectomy procedures, but can also be used for closed procedures in which, for example, imaging studies have proven that there are annular tears or rents which reproduce concordant pain. Installation of the biocompatible alloplastic implant, in accordance with one implementation of the present invention, may be especially suited for annular tears which are not asymptomatic and which do not produce discordant pain.

Implantation of the biocompatible alloplastic implant, if performed in the context of a closed procedure, can be accomplished from a posterior midline or posterolateral approach or a direct lateral approach. If performed in the context of an open procedure, implantation of the biocompatable alloplastic implant can be achieved from a posterior midline approach, posterolateral approach, anterior, anterolateral, or direct lateral approach. It is therefore possible that if an anterior approach is being utilized for an anterior diskectomy alone, the biocompatible alloplastic implant of the present invention can be instilled through a syringe and needle into that nucleus pulposus space after, for example, an offending spinal disk fragment or fragments have been removed. In certain implementations, the material can be introduced via flexible catheters of variable length and diameter, such as, for example, standard percutaneous needles and standard catheter tips known in the industry. In an exemplary open procedure where for example a laminectomy or microdiscectomy is being performed, it may be easier to inject the biocompatable alloplastic implant as used according to the present invention with the aid of an injection syringe, such as a 25-gauge syringe with a 3 or 4" needle.

The maturation of the biocompatible alloplastic implant of the present invention, in accordance with an aspect of the present invention, can over time afford additional, or at least partial, stabilization to the annulus fibrosis which can then provide additional support to the motion segment involved. This change in the biomechanics can translate into a partial increase in the stability for this motion segment. Having an annular tear generally can cause a weakening in the supporting structure of the motion segment. Treating the nucleus pulposus of a spinal disk with the biocompatible alloplastic implant of the present invention can in certain implementations allow a maximum amount of the nuclear material to remain centrally located and/or can increase the integrity of the surrounding annular fibers.

The biocompatable alloplastic implant of the present invention preferably comprises a plurality of microparticles, which can comprise solid microparticles in representative embodiments. In modified implementations, the microparticles may not be altogether solid, such as implementations involving hollow or porous microparticles. As used herein, the term "microparticles" refers to microparticles (e.g., in a dust or powder form) possessing an average diameter of 500 microns or less. Typically, the average diameter will be greater than about 20 microns rendering the microparticles too large to be "eaten" by monocytes. The microparticles can have diameters sufficient to keep them from being washed away through lymph tracts or other tissue tracts from the implantation site. If the microparticles do not have a spherical form, then the diameter as used herein refers to the greatest diameter of the smallest cross sectional area. It is, however, also possible to use smaller microparticles ranging from 4 to 5 microns or 5 to 10 microns in diameter. Typically, the microparticles will have an average diameter less than about 200 microns. In representative embodiments, the microparticles can have an average diameter of about 15 to about 200 microns and in certain implementations from about 15 to about 60 microns. In representative configurations, the microparticles are small enough to be injected through a fine gauge cannula (e.g., 25 gauge) or an injection syringe to the desired spinal disk region. Particles having the diameters specified herein may have a relatively minimal effect on the surrounding tissues, i.e., the dura of the cal sac or nerve root sleeves.

Due to the formed surface and size of the microparticles used, they are not detected by the endogenous macrophages as foreign bodies so that no defensive reaction takes place. According to a representative embodiment, the microparticles have spherical forms or spherical-like forms capable of forming closely-packed arrangements at the site where they have been implanted and further capable of being individually encapsulated by the scar tissue.

During a conventional provocative CT diskography, opening spinal-disk pressures are often measured. In the context of diskography, or any of the above-mentioned procedures, it is possible in accordance with certain aspects of the present invention for a spinal-disk opening pressure to be significantly altered by the introduction of the biocompatible alloplastic implant into the nucleus pulposus of that spinal disk and, preferably, into a central region of the nucleus pulposus, so that, for example, at least partial sealing of the spinal disk can be effectuated from the inside out.

As a result of implantation of the biocompatable alloplastic implant into a spinal disk, a seal or occlusion can be formed in the annulus fibrosis defect via, for example, in one implementation, displacement of nucleus pulposus from the site of implantation (e.g., an intermediate or, more preferably in some embodiments, central region of the nucleus pulposus) in a direction toward, for example, an annulus fibrosis defect, so that nucleus pulposus is displaced into a vicinity of the annulus fibrosis defect thus serving to strengthen or otherwise affect at least one property of the spinal disk or defect. In another implementation of the present invention, a seal or occlusion can be formed in the annulus fibrosis defect via, for example, introduction of the biocompatable alloplastic implant into the nucleus pulposus in a direct or proximate vicinity of the annulus fibrosis defect thus serving to enhance or otherwise affect at least one property of the spinal disk or defect. For instance, if the biocompatible alloplastic implant is injected or inserted in either a closed fashion or an open fashion, and if a sufficient portion of the biocompatible alloplastic implant is placed (and/or caused to solidify or mature) in the center, increased nuclear support can ensue giving rise to not only an increased annular integrity but also, for example, an increased nuclear stability.

The microparticles, which in a representative embodiment may comprise PMMA spherical beads, after being inserted into the spinal disk space, may be encapsulated by delicate capsules of connective tissue and/or are embedded into connective-tissue tissue or fibers and remain stationary in the tissue. Use of a suspending agent as described herein is not mandatory since the microparticles can be inserted (e.g., placed) or injected also without a suspending agent into the body.

Once placed into the nucleus pulposus, the biocompatible alloplastic implant may mimic or provide a substitute for at least one characteristic of the physiologic structure of the spinal disk. For example, the biocompatible alloplastic implant may mimic the spinal disk and operate as a partial artificial disk or operate as a partial artificial nucleus pulposus. Accordingly, a morphology of a disco gram may be improved following implantation of the biocompatible alloplastic implant. For instance, the accumulation of the microparticles of the biocompatable alloplastic implant and/or the accumulation of scar tissue around the microparticles within the nucleus pulposus can impart a certain physical stability to the interior of the spinal disk and/or to exterior portion of the annulus fibrosis. Later testing after the sealant (i.e., the biocompatable alloplastic implant) has matured (e.g., been incorporated into the host tissue through, for example, formation of permanent scar tissue around the microparticles of the implant) can yield an increase in the pressure gradient of the nucleus pulposus. Also, a slight increase in spinal disk space height may be achieved in proportion to the amount of the biocompatible alloplastic implant instilled which may vary from spinal disk to spinal disk, but which in a representative embodiment does not exceed about 3 to 4 cubic centimeters (ccs) and, typically, is within a range of about 0.5 to 1.5 ccs. During injection, it is advantageous to release pressure on the syringe plunger when the tip of the needle is within about 3-5 mm from the outer surface of the disk during removal of the needle from the disk.

Regarding maturation of the microparticles, which in a representative embodiment may comprise PMMA spherical beads, as a result of the size and physical stability of the PMMA beads, they cannot be phagocytised or lysed. In order to isolate the foreign body, the animal body can only fibrotically wall off the foreign bodies in the form of scar tissue. Such a process takes place with almost any foreign body which cannot be destroyed by the animal body. Prior to or substantially commensurate in time with installation of the biocompatible alloplastic implant and any removal of a part of the spinal disk (if applicable), the annular fibers that are attached to the vertebra end plates above and below can be minimally resected to allow punctate bleeding to occur from, for example, the edges of the end plate.

To the extent present, the fibrotic growth of connective tissue is a natural reaction to the lesion of the tissue caused by the injection cannula and to the presence of the microparticles. The fibrotic reaction may occur during 3-6 months after injection of the biocompatable alloplastic implant due to the smooth and chemically inert surfaces of the microparticles (e.g., PMMA beads). From then on, the beads remain in the tissue without reaction and provide for the formation and existence of permanent fibrovascular connective tissue.

The biocompatible alloplastic implant can in one implementation comprise a histocompatible solid in the form of a powder. The microparticles forming the solid may be incorporated into a suspending agent and injected, for instance, with an injection needle at the desired spinal disk level.

It can be advantageous for the microparticles used according to an embodiment of the present invention to have a smooth surface and be free from corners and edges, such that the microparticles don't have sharp transitions on their surfaces. In addition they may not have peaks of any kind or tapered projections. According to one implementation, the surface does not have pores. In another implementation, the surfaces may comprise pores. Although smooth, and especially spherical particles can be advantageous, in some embodiments, non-smooth microparticles of with corners or peaks or the like may still be used in the present spinal disk treatment application.

In many advantageous embodiments, the transition from one outer surface to the other outer surface of the microparticles as used according to the present invention occurs in a continuous manner. If such transitions are present, as is the case for the edges of a cube, such transitions may be smoothed. According to an embodiment of the present invention, microparticles which are crystalline (for instance needle-shaped) or microparticles which have been obtained by mechanically breaking up greater units into small pieces, are not used to the extent the microparticles possess the above-mentioned sharp edges and corners. Due to the smooth surface structure damage to cells and other tissue structures is minimized. In addition, the danger of causing reactions of the tissue, such a foreign body reactions or granulous formation, which may be followed by infections, is minimized.

In one implementation, dynamically balanced microparticles and in particular microparticles having an elliptic or spherical form can be used. In addition, it is possible to use microparticles of a different geometrical form if all, or in another embodiment, a majority, of the microparticles have a smooth and smoothed-off surface.

The inert, histocompatible material of the microparticles used according to representative embodiments of the present invention can comprise plexi-glass (or "bone cement") which is present in the form of plexi-glass beads or plexi-glass pellets having a smooth and/or smoothed off surface. The microparticles used, according to representative implementations of the present invention, can comprise a polymer, and in particular a completely cured and fully polymerised polymer so that no remaining monomers, which may be toxic or may cause cancer, are incorporated into the body of the treated patient.

In principle, it is possible to use any inert histocompatible polymer for producing the microparticles used according to the present invention. Modified embodiments may comprise, in whole or in part, non-polymer microparticles. In an exemplary embodiment, the implant comprises one or more of the implants described under the name Artecoll® and obtainable at www.artecoll.com and www.canderm.com. Exemplary embodiments are also described in the U.S. Pat. No. 5,344,452, the entire contents of which is incorporated herein by reference.

The implant material may comprise, for example, about 20% substantially smooth spherical PMMA beads ranging in size from about 32-40 micrometer diameter, and with low levels of methylmethacrylate monomer impurities. The remaining 80% may comprise a solution of partially denatured collagen, which may be about 3.5% collagen in a solution of water and/or alcohol. In one embodiment, there are about 6 million particles per cc of implant material.

Fully polymerised PMMA is histocompatible and can be incorporated in the human body without harmful toxic or carcinogenic reactions so that it can be considered as chemically and physically inert and biocompatable. For these reasons, PMMA polymers have already been used for manufacturing implants such as bone cement for the plastic covering of bone defects in the face and in the cranium, or as in a total hip or total knee arthroplasty. The polymer is also being used for manufacturing artificial teeth, as artificial heart valves and for manufacturing intra-ocular lenses and dialysis membranes.

To inject the microparticles or polymer microparticles used according to the present invention as an implant in a spinal disk, the microparticles can be formed within a suspending agent. A gel which is known per se, and is degraded within the body, for instance, on the basis of gelatin or, preferably, collagen, can be used as a suspending agent. The suspending agent used according to one implementation of the present invention can comprise a tenside, such as Tween ad, since such a tenside changes the surface tension of water so that the microparticles, and in particular embodiments, the polymer microparticles, have a more uniform distribution.

The mixing ratio of the components of the suspending agent can be chosen according to the needs, and in particular according to the size of the syringe used for the injection. For the application or injection of the microparticles used according to an embodiment of the present invention, the microparticles can be suspended or slurried in a fluid inert medium. In one particular implementation, a ratio of two volume parts of the suspending agent and one volume part of the microparticles or polymer microparticles is chosen.

Additionally, medical kits may be produced containing elements necessary for treating and/or repairing tendons and ligaments with the tissue-promoting implant. Such a kit may include a quantity of the implant, and a delivery device, such as a syringe or other applicator. One or more surgical tools used in conventional spinal disk access and repair surgery are also advantageously provided in such kits.

It will be appreciated that the invention has a variety of aspects. In accordance with some of these aspects, a biocompatible alloplastic implant can be utilized for annular welding or sealing of a spinal disk defect, such as a ruptured spinal disk. The biocompatible alloplastic implant can include solid microparticles which have smooth surfaces that are substantially free from corners and edges and which can in certain implementations be suspended in a biocompatible medium. The biocompatible alloplastic implant can be inserted into a ruptured spinal disk, filling a portion of the nucleus pulposus or annulus fibrosis and providing a seal. In one implementation, the biocompatible alloplastic implant is inserted into a central region of the ruptured spinal disk. Insertion of the biocompatible alloplastic implant into the ruptured spinal disk can attenuate a risk for recurrent spinal disk herniation and restore at least a portion of a structural integrity or shock absorbing capacity of the spinal disk.

A method of treating a spinal disk according to the present invention can comprise identifying a defect in a spinal disk and inserting an alloplastic bulking agent into the spinal disk to thereby treat the defect, wherein the alloplastic bulking agent comprises a plurality of microparticles. The identifying of a defect can comprise, for example, identifying a defect through a scope. In typical implementations, the identifying of a defect can comprise identifying a focal outpouching comprising a displacement of nucleus pulposus within a partially torn or thinned annulus fibrosis of the spinal disk, can comprise identifying an extrusion comprising displaced nucleus pulposus which remains in continuity with an interior of the spinal disk through a rent in an annulus fibrosis of the spinal disk, or can comprise identifying a sequestration comprising displaced nucleus pulposus which does not remain in continuity with an interior of the spinal disk.

The microparticles can be histocompatible with smooth surfaces free from corners and edges, can be dynamically balanced, and can have at least one of elliptical and spherical forms. For example, the plurality of microparticles typically can comprise a plurality of microspheres, which can be inserted into the spinal disk as loose microparticles and remain therein as loose microparticles. In representative embodiments, the microparticles have diameters such that they cannot be washed away from lymph tracts or other tissue tracts from the implantation site. A majority of the microparticles can have diameters of at least 10 microns, and in certain implementations the microparticles can have an average diameter within a range of about 15 to about 200 microns. The microparticles, further, can have diameters from about 15 to about 60 microns.

As for composition, the microparticles in accordance with certain implementations of the present invention can comprise a cured polymer, such as a polymethacrylate or a polymethylmethacrylate (PMMA). In one implementation, the microparticles can comprise solid microparticles, which may take the form in one embodiment of non-porous beads that may be disposed in a physiologically biocompatible suspending agent. The suspending agent can be a liquid and can comprise at least one of water and saline. In certain implementations, the suspending agent can be one of a collagen and a gelatin that is degradable in a mammalian body. Furthermore, the suspending agent can be admixed with a tenside.

The inserting can comprise inserting an alloplastic bulking agent into the spinal disk while viewing at least a part of the spinal disk through a scope. The scope can comprise a video fluoroscope, and the inserting can be fluoroscopically guided. In one implementation, the alloplastic bulking agent can be impregnated with a water soluble radiopaque dye to facilitate visualization during the inserting of the alloplastic bulking agent into the spinal disk. The radiopaque dye can comprise barium. In a typical implementation, the inserting can comprise inserting about 3 or 4 cubic centimeters (ccs) or less of the alloplastic bulking agent into a nucleus pulposus of the spinal disk, and in certain implementations the inserting comprises inserting about 0.5 to 1.5 cubic centimeters (ccs) of the alloplastic bulking agent into the nucleus pulposus of the spinal disk.

The inserting may be followed by a height of the spinal disk being increased, wherein the increase in height is proportional to an amount of the alloplastic bulking agent inserted into the spinal disk. In accordance with one aspect of the present invention, the inserting may be followed by a structural integrity of the spinal disk being improved, compared to a structural integrity of the spinal disk before the inserting. For example, a stability of the annulus fibrosis of the spinal disk may be improved relative to a stability of the annulus fibrosis before the inserting, whereby a biomechanical property of a motion segment of the spinal disk is improved compared to biomechanical property of the motion segment before the inserting.

When the spinal disk is juxtapositioned in proximity to at least one of an upper vertebra and a lower vertebra, at least one aperture can be formed in an endplate of one or both of the upper vertebra and the lower vertebra. Typically, the spinal disk is juxtapositioned between an upper vertebra and a lower vertebra, and a plurality of apertures are formed in an endplate or endplates of at least one of the upper vertebra and the lower vertebra. The aperture or apertures can be formed using a needle, which may already be present in the spinal disk during an ongoing procedure such as, for example, a diskography procedure.

In representative implementations of the methods disclosed herein, the defect comprises a spinal annular defect. For instance, the defect can comprise an internal disk derangement. Insertion of the alloplastic bulking agent into the spinal disk can cause a seal to be formed in and around the spinal annular defect. This seal can create a more stable motion segment of the spinal disk compared to a motion segment of the spinal disk before the inserting, by for example imparting increased stability to the spinal disk relative to a stability of the spinal disk before the inserting.

The inserting can be performed during a diskography procedure, and the defect can comprise at least one annular rent. During the diskography procedure, the identifying can comprise an initial visualization of the at least one rent followed by the inserting being performed during the same diskography procedure. In accordance with one implementation of the inventive methods disclosed herein, the diskography procedure comprises a provocative diskography procedure wherein the identifying comprises an initial visualization of the at least one rent and wherein the inserting is performed during the same provocative diskography procedure.

According to another implementation, the diskography procedure can be performed percutaneously through one of a posterior, posterolateral, lateral, anterior or anterolateral approach to the spinal disk.

In other implementations, the inserting can be performed during an open procedure, and can comprise inserting the alloplastic bulking agent using a syringe and needle into the spinal disk in one of a laminotomy, laminectomy, hemilaminotomy and hemilaminectomy open procedure.

Another method of the present invention that can be performed on a spinal disk includes delivering a bulking material comprising a plurality of microparticles into a spinal disk. The delivering can be preceded by inserting an injection device into the spinal disk, and the bulking material can be delivered though the injection device and into the spinal disk. When the spinal disk is positioned in proximity to at least one of an upper vertebra endplate and a lower vertebra endplate, the method can comprise forming one or more apertures or perforations in at least one of the upper vertebra endplate and the lower vertebra endplate.

The delivering of a bulking material can comprise delivering a bulking material into a nucleus pulposus of the spinal disk, such as an central or non-perimeter region of the spinal disk. The delivering can be preceded by detecting a condition in the spinal disk, and the bulking material can be delivered into the spinal disk to treat the condition. Furthermore, the microparticles can be shaped as, for example, microspheres, and can be uniformly distributed in a suspending agent, such as a suspending agent comprising collagen. Moreover, the detecting of a condition can comprise detecting a displacement of inner disk material within a partially torn or thinned annulus of the spinal disk, and the delivering can comprise delivering an amount on the order of about 3 to 4 cubic centimeters (ccs) or less of the bulking material into the spinal disk.

It may also be noted that the techniques described herein can be used to advantageous effect for treating household pets such as dogs and cats. In these cases, vertebral fusions and similar procedures are often cost prohibitive, so any lower cost techniques for disk repair would be beneficial.

The above-described embodiments have been provided by way of example, and the present invention is not limited to these examples. Multiple variations and modifications to the disclosed embodiments will occur, to the extent not mutually exclusive, to those skilled in the art upon consideration of the foregoing description. Additionally, other combinations, omissions, substitutions and modifications will be apparent to the skilled artisan in view of the disclosure herein. Accordingly, the present invention is not intended to be limited by the disclosed embodiments.

What is claimed is:

1. A method of sealing an annular tear or fissure in an annulus fibrosis during a discography procedure comprising:
    performing a discography procedure on a spinal disk;
    detecting the annular tear or fissure in the discography procedure;
    after the detecting, delivering a biocompatible agent to an interior portion of the spinal disk inside the annulus fibrosis into or proximate the annular tear or fissure such that the biocompatible agent seals the annular tear or fissure;
    after the delivering, incorporating the biocompatible agent into host tissue through formation of permanent tissue proximate the biocompatible agent;
    wherein the biocompatible agent comprises a plurality of microparticles, the microparticles each having a diameter in the range of 5 to 500 microns.

2. The method of claim 1, further comprising at least one of increasing a pressure of the disk, increasing a height of the disk, improving stability of the disk and improving structural integrity of the disk.

3. The method of claim 1, wherein the agent comprises at least one of water, saline, a tenside, radiopaque dye, and a chromophobe.

4. The method of claim 1, wherein said microparticles comprise one or more of poly methacrylate, polymethylmethacrylate (PMMA), a cured polymer, a fully polymerized polymer, and glass.

5. The method of claim 1, wherein delivering the agent comprises viewing the spinal disk through a scope.

6. The method of claim 1, wherein delivering the agent comprises delivering 0.5 to 1.5 cubic centimeters of the agent.

7. The method of claim 1, wherein delivering the agent comprises delivering the agent to a nucleus pulposus of the disk.

* * * * *